United States Patent
Poslavsky et al.

(10) Patent No.: US 9,347,872 B1
(45) Date of Patent: May 24, 2016

(54) META-MODEL BASED MEASUREMENT REFINEMENT

(71) Applicant: KLA-Tencor Corporation, Milpitas, CA (US)

(72) Inventors: Leonid Poslavsky, Belmont, CA (US); Lie-Quan Lee, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/493,863

(22) Filed: Sep. 23, 2014

Related U.S. Application Data

(60) Provisional application No. 61/881,198, filed on Sep. 23, 2013.

(51) Int. Cl.
*G01B 11/28* (2006.01)
*G01N 21/21* (2006.01)

(52) U.S. Cl.
CPC ........ *G01N 21/211* (2013.01); *G01N 2021/213* (2013.01); *G01N 2201/06113* (2013.01)

(58) Field of Classification Search
USPC ............................. 356/625–640, 237.1–237.6
See application file for complete search history.

(56) References Cited

U.S. PATENT DOCUMENTS

2009/0196477 A1* 8/2009 Cense .................... A61B 3/102
  382/131
2009/0261848 A1* 10/2009 Araki et al. .................. 324/705

* cited by examiner

*Primary Examiner* — Tri T Ton
(74) *Attorney, Agent, or Firm* — Spano Law Group; Joseph S. Spano

(57) ABSTRACT

Methods and systems for determining a meta-model to correct model based measurements are presented. Such systems are employed to measure structural and material characteristics (e.g., material composition, dimensional characteristics of structures and films, etc.) associated with different semiconductor fabrication processes. In one aspect, model-based measurement parameter values are corrected based on a meta-model that maps specimen parameter values determined based on the measurement model to reference parameter values determined based on a more accurate reference measurement. In another aspect, parameters of a meta-model are determined such that errors between reference parameter values and specimen parameter values determined based on the measurement model are minimized. In some embodiments, the accuracy of a corrected parameter value is an order of magnitude greater than the uncorrected parameter value.

20 Claims, 4 Drawing Sheets

META-MODEL BASED MEASUREMENT REFINEMENT

CROSS REFERENCE TO RELATED APPLICATION

The present application for patent claims priority under 35 U.S.C. §119 from U.S. provisional patent application Ser. No. 61/881,198, entitled "Post-Library Generation Improvement Through Meta-Modeling," filed Sep. 23, 2013, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

In response to these challenges, more complex optical tools have been developed. Measurements are performed over a large ranges of several machine parameters (e.g., wavelength, azimuth and angle of incidence, etc.), and often simultaneously. As a result, the measurement time, computation time, and the overall time to generate reliable results, including measurement recipes, increases significantly.

In addition, existing model based metrology methods typically include a series of steps to model and then measure structure parameters. Typically, measurement data (e.g., DOE spectra) is collected from a particular metrology target. An accurate model of the optical system, dispersion parameters, and geometric features is formulated. In addition, simulation approximations (e.g., slabbing, Rigorous Coupled Wave Analysis (RCWA), etc.) are performed to avoid introducing excessively large errors. Discretization and RCWA parameters are defined. A series of simulations, analysis, and regressions are performed to refine the geometric model and determine which model parameters to float. A library of synthetic spectra is generated. Finally, measurements are performed using the library and the geometric model. Each step introduces errors and consumes a significant amount of computational and user time. The size of the library and the computation time associated with performing regression calculations during measurement reduces the throughput of the measurement system. Often, simplifying assumptions are introduced to maintain throughput, however, these simplifications often introduce undesirable measurement errors.

Maintaining measurement accuracy with sufficient throughput is a core challenge in the development of an optical metrology system that meets customer requirements of the semi-conductor industry. Thus, methods and systems for improved measurement accuracy with high throughput are desired.

SUMMARY

Methods and systems for determining a meta-model and correcting model based measurements with the meta-model are presented. Such systems are employed to measure structural and material characteristics (e.g., material composition, dimensional characteristics of structures and films, etc.) associated with different semiconductor fabrication processes.

In one aspect, model-based measurement parameter values are corrected based on a meta-model that maps specimen parameter values determined based on the measurement model to reference parameter values determined based on a more accurate reference measurement. In some embodiments, the accuracy of a corrected parameter value is an order of magnitude greater than the uncorrected parameter value.

In another aspect, parameters of a meta-model are determined such that errors between reference parameter values and specimen parameter values determined based on the measurement model are minimized.

In some examples, one or more specimen parameter values are estimated based on measurement data derived from actual measurements. In some other examples, one or more specimen parameter values are estimated based on synthetic measurement data.

In some examples, one or more reference parameter values are estimated based on reference measurement data derived from actual measurements. In some other examples, one or more reference parameter values are estimated based on synthetic measurement data.

In some examples, one or more reference parameter values are estimated using a reference library function that is more accurate than a library function employed to estimate the specimen parameter values from measurement data. Similarly, in some examples, one or more reference parameter values are estimated using a regression of a reference measurement model that is more accurate than the measurement model used to estimate the specimen parameter values.

In some other examples, the measurement data set employed to determine the specimen parameter values is a subset of the reference measurement data employed to determine the reference parameter values. For example, the reference measurement data may include measurement data over a range of wavelengths, azimuth angle, polarization, etc. In this manner, more accurate reference parameter values are determined based on a relatively rich data set. In contrast, the measurement data set is a subset of the reference measurement data (e.g., a single wavelength, azimuth angle, polarization, etc.) that yields an estimate of one or more specimen parameter values with less accuracy.

In some examples, the reference measurement source is a fleet of measurement systems. In these examples, the reference parameter values are determined based on measurement data from each measurement system in the fleet of measurement systems.

In yet another example, the reference measurement source is another measurement technology (e.g., a direct measurement technology such as a transmission electron microscope, an atomic force microscope, etc.) that is capable of measuring specimen parameter values with greater accuracy than the target measurement system.

In some examples, the reference measurement source is a similar tool that is treated as a reference tool (or "golden" tool). Measurements from a "golden" tool are treated as the desired measurement output for a particular specimen parameter.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for determining a meta-model and correcting model based measurements with the meta-model are presented. Such systems are employed to measure structural and material characteristics (e.g., material composition, dimensional characteristics of structures and films, etc.) associated with different semiconductor fabrication processes.

Figure 1:
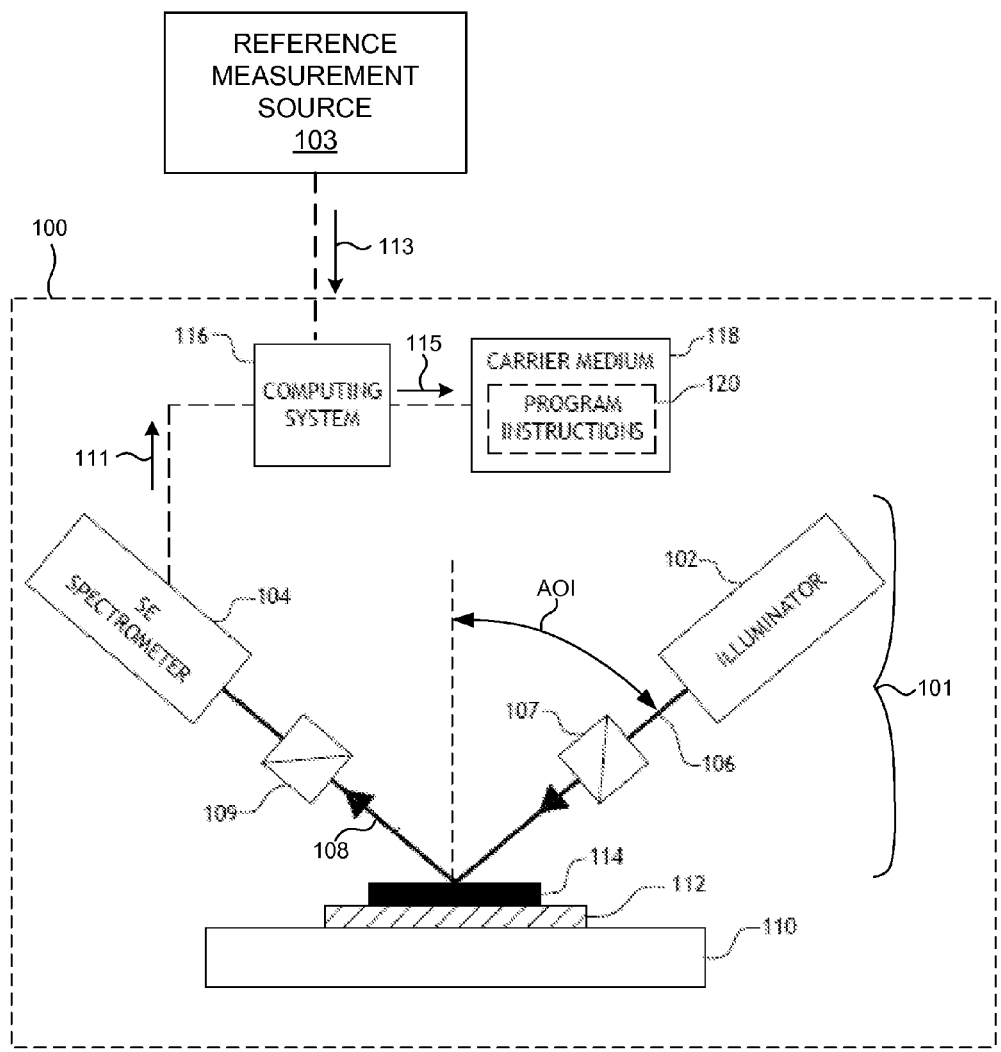
FIG. 1 is a diagram illustrative of a metrology system 100 configured to implement the meta-model based measurement correction methods described herein.

FIG. 1 illustrates a system 100 for measuring characteristics of a semiconductor wafer in accordance with the exemplary methods presented herein. As shown in FIG. 1, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-1700 nm) to the structure 114 disposed on the surface of the semiconductor wafer 112. In turn, the spectrometer 104 is configured to receive light from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis by the spectrometer of radiation passed by the analyzer. These spectra 111 are passed to the computing system 116 for analysis of the structure 114.

In a further embodiment, the metrology system 100 is a target measurement system 100 that may include one or more computing systems 116 employed to determine a meta-model and correct measured parameter values of the structure 114 based on the meta-model in accordance with the methods described herein. The one or more computing systems 116 may be communicatively coupled to the spectrometer 104. In one aspect, the one or more computing systems 116 are configured to receive measurement data 111 associated with a measurement (e.g., critical dimension, film thickness, composition, process, etc.) of the structure 114 of specimen 112. In one example, the measurement data 111 includes an indication of the measured spectral response of the specimen by target measurement system 100 based on the one or more sampling processes from the spectrometer 104. In some embodiments, the one or more computing systems 116 are further configured to determine specimen parameter values of structure 114 from measurement data 111. In one example, the one or more computing systems 116 are configured to access model parameters in real-time, employing Real Time Critical Dimensioning (RTCD), or it may access libraries of pre-computed models for determining a value of at least one specimen parameter value associated with the target structure 114.

In addition, in some embodiments, the one or more computing systems 116 are further configured to receive a set of reference parameter values 113 associated with a measurement of the structure 114 by a reference measurement source 103. In some examples, the set of parameter values is stored in carrier medium 118 and retrieved by computing system 116.

The one or more computer systems are further configured to determine one or more parameters of a meta-model function that approximately maps the measurement parameter values to the reference parameter values.

The one or more computer systems are further configured to receive one or more measured parameter values associated with one or more structures of a specimen under measurement and determine one or more corrected parameter values based at least in part on a transformation of the one or more measured parameter values by the meta-model function.

In some embodiments, target measurement system 100 is further configured to store the one or more corrected parameter values 115 in a memory (e.g., carrier medium 118).

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, the one or more computing systems 116 may be configured to perform any other step(s) of any of the method embodiments described herein.

In addition, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other block(s) of any of the method embodiment(s) described herein.

As illustrated in FIG. 1, a beam of broadband radiation from illuminator 102 is linearly polarized in polarization state generator 107, and the linearly polarized beam is then incident on specimen 112. After reflection from specimen 112, the beam propagates toward polarization state analyzer 109 with a changed polarization state. In some examples, the reflected beam has elliptical polarization. The reflected beam propagates through polarization state analyzer 109 into spectrometer 104. In spectrometer 104, the beam components having different wavelengths are refracted (e.g., in a prism spectrometer) or diffracted (e.g., in a grating spectrometer) in different directions to different detectors. The detectors may be a linear array of photodiodes, with each photodiode measuring radiation in a different wavelength range.

In one example, computing system 116 receives the measured data from each detector, and is programmed with software for processing the data it receives in an appropriate manner. The measured spectral response of a specimen may be determined by analyzing the changes in polarization of radiation reflected from the sample in response to incident radiation having known polarization state in any number of ways known in the art.

Any of polarization state generator 107 and polarization state analyzer 109 may be configured to rotate about their optical axis during a measurement operation. In some examples, computing system 116 is programmed to generate control signals to control the angular orientation of polarization state generator 107 and/or polarization state analyzer 109, or other elements of the system 100 (e.g., wafer positioning system 110 upon which specimen 112 rests). Computing system 116 may also receive data indicative of the angular orientation of polarization state analyzer 109 from an analyzer position sensor associated with polarization state analyzer 109. Similarly, computing system 116 may also receive data indicative of the angular orientation of polarization state generator 107 from a polarizer position sensor associated with polarization state generator 107. Computing system 116 may be programmed with software for processing such orientation data in an appropriate manner.

In one embodiment, the polarization state generator 107 is a linear polarizer that is controlled so that it rotates at a constant speed, and the polarization state analyzer is a linear polarizer that is not rotating ("the analyzer"). The signal received at each detector of spectrometer 104 will be a time-varying intensity given by:

$$I(t)=I_0[1+\alpha \cos(2\omega t-P_0)+\beta \sin(2\omega t-P_0)] \quad (1)$$

where $I_0$ is a constant that depends on the intensity of radiation emitted by illuminator 102, $\omega$ is the angular velocity of polarization state generator 107, $P_0$ is the angle between the optical axis of polarization state generator 107 and the plane of incidence (e.g., the plane of FIG. 1) at an initial time (t=0), and $\alpha$ and $\beta$ are values defined as follows:

$$\alpha=[\tan^2\Psi-\tan^2(A-A_0)]/[\tan^2\Psi+\tan^2(A-A_0)] \quad (2)$$

and $$\beta=[2(\tan \Psi)(\cos \Delta)(\tan(A-A_0))]/[\tan^2\Psi+\tan^2(A-A_0)] \quad (3)$$

where $\tan(\Psi)$ is the amplitude of the complex ratio of the p and s reflection coefficients of the sample and $\Delta$ is the phase of the complex ratio of the p and s reflection coefficients of the sample. The "p" component denotes the component of polarized radiation whose electrical field is in the plane of FIG. 1, and "s" denotes the component of polarized radiation whose electrical field is perpendicular to the plane of FIG. 1. A is the nominal analyzer angle (e.g., a measured value of the orientation angle supplied, for example, from the above-mentioned analyzer position sensor associated with polarization state analyzer 109). $A_0$ is the offset of the actual orientation angle of polarization state analyzer 109 from the reading "A" (e.g., due to mechanical misalignment, $A_0$ may be non-zero).

From equations (1)-(3), values of $\alpha$ and $\beta$ may be determined based on a measurement of a particular specimen by inspection system 100. Hence, for a particular metrology target on a specimen, values $\alpha_{meas}$ and $\beta_{meas}$ are determined based on spectrometer data.

In general, ellipsometry is an indirect method of measuring physical properties of the specimen under inspection. In most cases, the measured values (e.g., $\alpha_{meas}$ and $\beta_{meas}$) cannot be used to directly determine the physical properties of the specimen. The nominal measurement process consists of parameterization of the structure (e.g., film thicknesses, critical dimensions, etc.) and the machine (e.g., wavelengths, angles of incidence, polarization angles, etc.). A model is created that attempts to predict the measured values (e.g., $\alpha_{meas}$ and $\beta_{meas}$). As illustrated in equations (4) and (5), the model includes parameters associated with the machine ($P_{machine}$) and the specimen ($P_{machine}$).

$$\alpha_{model} = f(P_{machine}, P_{specimen}) \quad (4)$$

$$\beta_{model} = g(P_{machine}, P_{specimen}) \quad (5)$$

Machine parameters are parameters used to characterize the inspection tool (e.g., ellipsometer 101). Exemplary machine parameters include angle of incidence (AOI), analyzer angle ($A_0$), polarizer angle ($P_0$), illumination wavelength, numerical aperture (NA), etc. Specimen parameters are parameters used to characterize the specimen (e.g., specimen 112 including structures 114). For a thin film specimen, exemplary specimen parameters include refractive index, dielectric function tensor, nominal layer thickness of all layers, layer sequence, etc. For measurement purposes, the machine parameters are treated as known, fixed parameters and one or more of the specimen parameters are treated as unknown, floating parameters.

In some examples, the floating parameters are resolved by an iterative process (e.g., regression) that produces the best fit between theoretical predictions and experimental data. The unknown specimen parameters, $P_{specimen}$, are varied and the model output values (e.g., a $\alpha_{model}$ and $\beta_{model}$) are calculated until a set of specimen parameter values are determined that results in a close match between the model output values and the experimentally measured values (e.g., $\alpha_{meas}$ and $\beta_{meas}$). In a model based measurement application such as spectroscopic ellipsometry on a CD specimen, a regression process (e.g., ordinary least squares regression) is employed to identify specimen parameter values that minimize the differences between the model output values and the experimentally measured values for a fixed set of machine parameter values.

In some examples, the floating parameters are resolved by a search through a library of pre-computed solutions to find the closest match. In a model based measurement application such as spectroscopic ellipsometry on a CD specimen, a library search process is employed to identify specimen parameter values that minimize the differences between pre-computed output values and the experimentally measured values for a fixed set of machine parameter values.

In a model-based measurement application, simplifying assumptions often are required to maintain sufficient throughput. In some examples, the truncation order of a Rigorous Coupled Wave Analysis (RCWA) must be reduced to minimize compute time. In another example, the number or complexity of library functions is reduced to minimize search time. These simplifying assumptions may lead to unacceptable errors in the estimation of measurement parameter values.

In one aspect, model-based measurement parameter values are corrected based on a meta-model that maps specimen parameter values determined based on the measurement model to reference parameter values determined based on a more accurate reference measurement. In some embodiments, the accuracy of a corrected parameter value is an order of magnitude greater than the uncorrected parameter value.

In another aspect, parameters of a meta-model are determined such that errors between reference parameter values and specimen parameter values determined based on the measurement model are minimized. In this aspect, the meta-model approximately maps the one or more specimen parameter values to the one or more reference parameter values.

Figure 2:
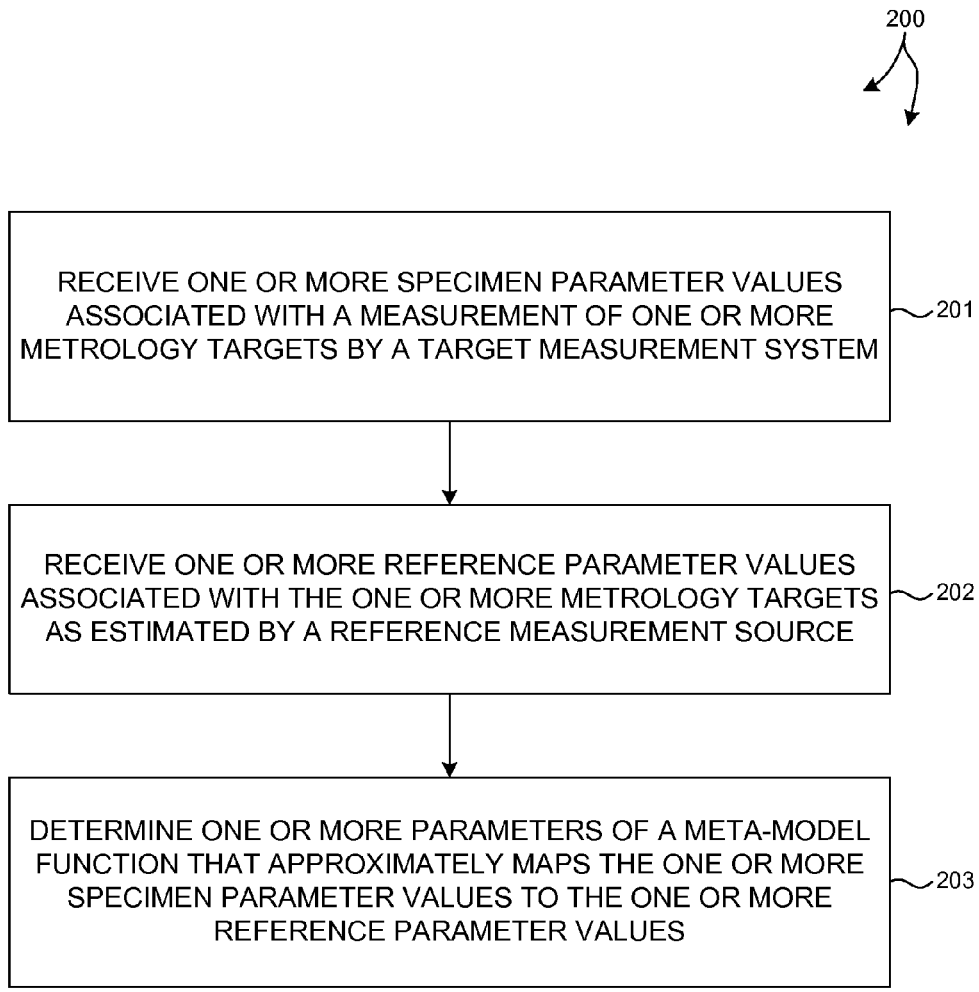
FIG. 2 is a flowchart illustrative of an exemplary method 200 of determining a meta-model suitable for measurement correction.

FIG. 2 illustrates a method 200 suitable for implementation by the metrology system 100 of the present invention. In one aspect, it is recognized that data processing blocks of method 200 may be carried out via a pre-programmed algorithm executed by one or more processors of computing system 116. While the following description is presented in the context of metrology system 100, it is recognized herein that the particular structural aspects of metrology system 100 do not represent limitations and should be interpreted as illustrative only.

In block 201, one or more specimen parameter values associated with a measurement of one or more metrology targets by a target measurement system are received. In one example, computing system 116 is configured to receive an indication of one or more specimen parameter values from a memory (e.g., carrier medium 118). In another example, computing system 116 is configured to receive an indication of one or more specimen parameter values directly from a target measurement system (e.g., ellipsometer 101). In this regard, there is no requirement that spectral acquisition and subsequent analysis of the spectral data need be contemporaneous or performed in spatial proximity. For instance, measurement data may be stored in memory for analysis at a later time. In another instance, measurement results may be obtained and transmitted to a computing system located at a remote location for analysis in accordance with the methods described herein.

In some examples, one or more specimen parameter values are estimated based on measurement data (e.g., $\alpha_{meas}$ and $\beta_{meas}$) derived from actual measurements. In some other examples, one or more specimen parameter values are estimated based on synthetic measurement data (e.g., measurement data generated by computer simulation).

In block 202, one or more reference parameter values (e.g., reference parameter values 113) are received, for example, by computing system 116. The reference parameter values are associated with a reference measurement of the one or more metrology targets. In one example, reference parameter values 113 are received by computing system 116 from a reference measurement source 103.

In some examples, one or more reference parameter values are estimated based on reference measurement data (e.g., $\alpha_{meas}$ and $\beta_{meas}$) derived from actual measurements. In some other examples, one or more reference parameter values are estimated based on synthetic measurement data (e.g., generated by computer simulation).

In some examples, one or more reference parameter values are estimated using a reference library function that is more accurate than a library function employed to estimate the specimen parameter values from measurement data. Similarly, in some examples, one or more reference parameter values are estimated using a regression of a reference measurement model that is more accurate that the measurement model used to estimate the specimen parameter values.

In one example, the target measurement system (e.g., ellipsometer 101) is also the reference measurement source. In these examples the reference measurement involves a more accurate measurement model or more complex library than the target measurement.

In another example, the reference measurement source is a fleet of measurement systems. In these examples, the reference parameter values are determined based on measurement data from each measurement system in the fleet of measurement systems. In one example, the reference parameter values are an average of the parameter values determined based on measurements from each measurement system in the fleet. In general, the reference parameter values can be determined based on any mathematical combination of parameter values determined based on measurements from each measurement system in the fleet (e.g., weighted average, mean, etc.).

In another example, the reference measurement source is another measurement technology (e.g., a direct measurement technology such as a transmission electron microscope, an atomic force microscope, etc.) that is capable of measuring specimen parameter values with greater accuracy than the target measurement system.

In yet another example, the measurement data set employed to determine the specimen parameter values is a subset of the reference measurement data employed to determine the reference parameter values. In some examples, the reference measurement data includes measurement data over a range of wavelengths, azimuth angle, polarization, etc. In this manner, more accurate reference parameter values are determined based on a relatively rich data set. In contrast, the measurement data set is a subset of the reference measurement data (e.g., a single wavelength, azimuth angle, polarization, etc.) that yields an estimate of one or more specimen parameter values with less accuracy.

In some examples, the reference measurement source is a similar tool that is treated as a reference tool (or "golden" tool). Measurements from a "golden" tool are treated as the desired measurement output for a particular specimen parameter.

In block 203, one or more parameters of a meta-model function are determined such that the meta-model maps the one or more specimen parameter values to the one or more reference parameter values.

Figure 4:
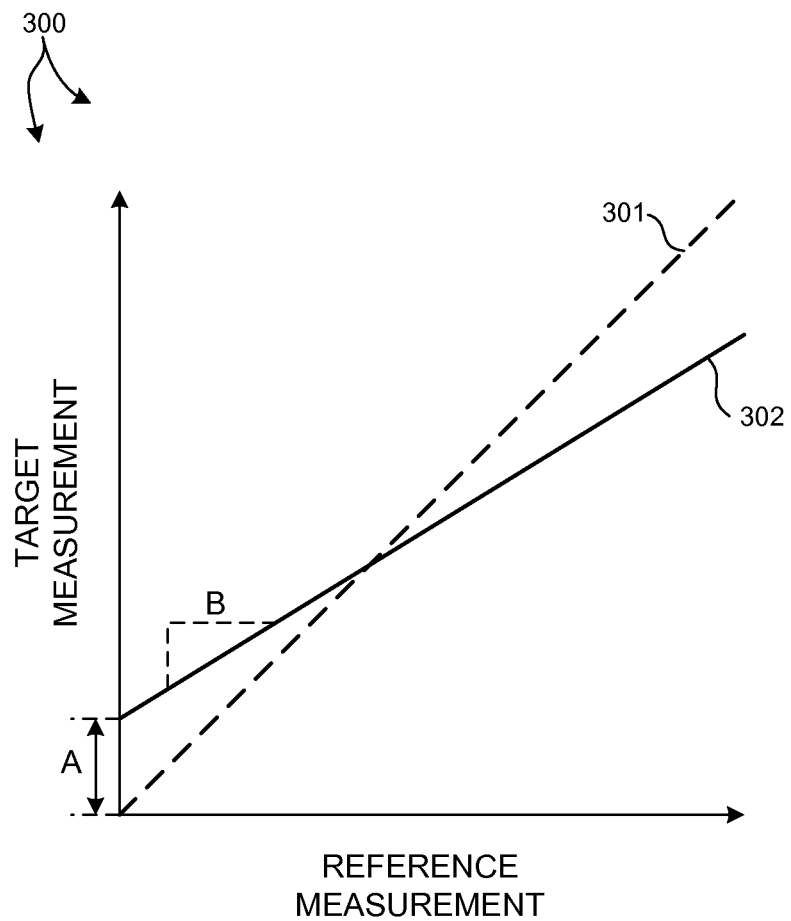
FIG. 4 is a plot 300 depicting a mismatch between parameter values determined by a target measurement and a reference measurement.

FIG. 4 illustrates a plot 300 depicting a line 302 of specimen parameter values determined by a target measurement system and a desired line 302 where specimen parameter values should lie if they matched reference parameter values perfectly. As depicted in FIG. 4, the specimen parameter values are misaligned with the reference parameter values by an offset, A, and a slope, B. In this simplified example, the parameters (e.g., A and B) of a meta-model function, f, can be determined to map the specimen parameter values to the reference parameter values as illustrated in Equation (6).

$$P_{corrected} = f(P_{specimen}) \quad (6)$$

In general, the mapping function, f, can be multi-dimensional and may be determined by any applicable linear or non-linear optimization technique (e.g., neural network, support vector machine, nonlinear least squares optimization, etc.).

Figure 3:
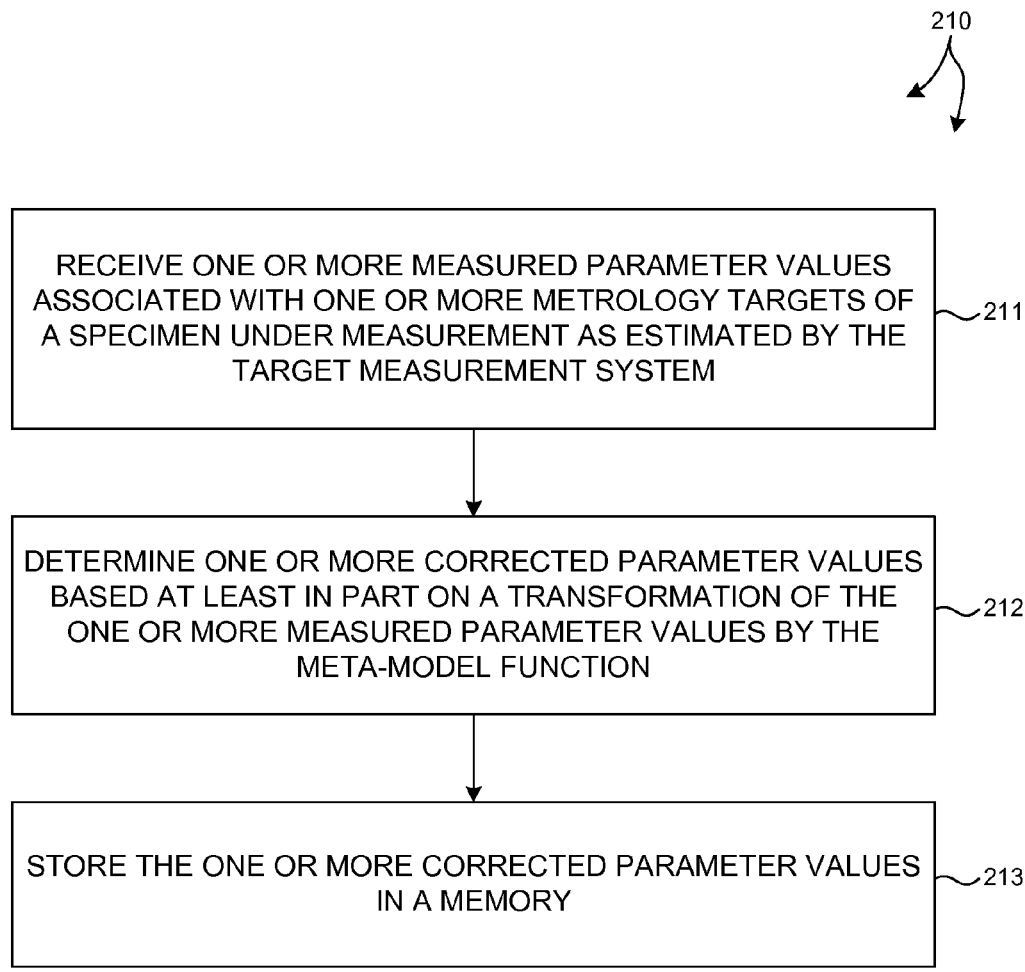
FIG. 3 is a flowchart illustrative of an exemplary method 300 of correcting a measurement using a meta-model function.

FIG. 3 illustrates a method 210 suitable for implementation by the metrology system 100 of the present invention. In one aspect, it is recognized that data processing blocks of method 210 may be carried out via a pre-programmed algorithm executed by one or more processors of computing system 116. While the following description is presented in the context of metrology system 100, it is recognized herein that the particular structural aspects of metrology system 100 do not represent limitations and should be interpreted as illustrative only.

In block 211, one or more measured parameter values associated with the measurement of one or more metrology targets of a specimen under measurement by a target measurement system are received, for example, by computing system 116.

In block 212, one or more corrected parameter values are determined based at least in part on a transformation of the one or more measured parameter values by the meta-model function (e.g., meta-model function, f, illustrated in Equation (6)).

In block 213, the one or more corrected parameter values are stored in a memory (e.g. carrier medium 120).

Although the methods discussed herein are explained with reference to system 100, any optical metrology system configured to illuminate and detect light reflected, transmitted, or diffracted from a specimen may be employed to implement the exemplary methods described herein. Exemplary systems include an angle-resolved reflectometer, a scatterometer, a reflectometer, an ellipsometer, a spectroscopic reflectometer or ellipsometer, a beam profile reflectometer, a multi-wavelength, two-dimensional beam profile reflectometer, a multi-wavelength, two-dimensional beam profile ellipsometer, a rotating compensator spectroscopic ellipsometer, etc. By way of non-limiting example, an ellipsometer may include a single rotating compensator, multiple rotating compensators, a rotating polarizer, a rotating analyzer, a modulating element, multiple modulating elements, or no modulating element.

It is noted that the output from a source and/or target measurement system may be configured in such a way that the measurement system uses more than one technology. In fact, an application may be configured to employ any combination of available metrology sub-systems within a single tool, or across a number of different tools.

A system implementing the methods described herein may also be configured in a number of different ways. For example, a wide range of wavelengths (including visible, ultraviolet, infrared, and X-ray), angles of incidence, states of polarization, and states of coherence may be contemplated. In another example, the system may include any of a number of different light sources (e.g., a directly coupled light source, a laser-sustained plasma light source, etc.). In another example, the system may include elements to condition light directed to or collected from the specimen (e.g., apodizers, filters, etc.).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), a displacement between two or more structures (e.g., overlay displacement between overlaying grating structures, etc.), and a dispersion property value of a material used in the structure or part of the structure. Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a site, or sites, on a wafer, a reticle, or any other sample that may be processed (e.g., printed or inspected for defects) by means known in the art. In some examples, the specimen includes a single site having one or more measurement targets whose simultaneous, combined measurement is treated as a single specimen measurement or reference measurement. In some other examples, the specimen is an aggregation of sites where the measurement data associated with the aggregated measurement site is a statistical aggregation of data associated with each of the multiple sites. Moreover, each of these multiple sites may include one or more measurement targets associated with a specimen or reference measurement.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
receiving measurement values of one or more specimen parameters associated with a model based measurement of one or more metrology targets by a target measurement system;
receiving reference measurement values of the same one or more specimen parameters associated with a measurement of the same one or more metrology targets by a reference measurement source that differs from the model based measurement of the one or more metrology targets by the target measurement system; and
determining one or more parameters of a meta-model that transforms the measurement values of the one or more specimen parameters to corrected measurement values of the one or more specimen parameters, wherein the determining of the one or more parameters of the meta-model involves minimizing a difference between the reference measurement values and the corrected measurement values of the one or more specimen parameters.

2. The method of claim 1, further comprising:
receiving measurement values of the same one or more specimen parameters associated with a model based measurement of another metrology target by the target measurement system;
determining corrected measurement values of the same one or more specimen parameters associated with the model based measurement of the other metrology target by the target measurement system based at least in part on a transformation of the received measurement values by the meta-model; and
storing the corrected measurement values of the same one or more specimen parameters associated with the model based measurement of the other metrology target in a memory.

3. The method of claim 1, wherein the measurement values of the one or more specimen parameters are estimated by the target measurement system based on any of an amount of synthetic measurement data and an amount of actual measurement data.

4. The method of claim 3, wherein the measurement values of the one or more specimen parameters are estimated by the target measurement system using any of a library function and a regression of a measurement model.

5. The method of claim 1, wherein the reference measurement values of the same one or more specimen parameters are estimated based on a measurement of the same one or more specimen parameters by a reference measurement system.

6. The method of claim 3, wherein the reference measurement values of the same one or more specimen parameters are estimated based on any of an amount of synthetic reference measurement data and an amount of actual reference measurement data.

7. The method of claim 6, wherein the reference measurement values of the same one or more specimen parameters are estimated using any of a reference library function and a regression of a reference measurement model.

8. The method of claim 7, wherein the measurement values of the one or more specimen parameters are estimated by the target measurement system based on an amount of measurement data that is a subset of an amount of reference measurement data.

9. The method of claim 1, wherein the determining of the one or more parameters of the meta-model involves any of a neural network optimization, a support vector machine optimization, and a nonlinear least squares optimization.

10. A non-transitory, computer-readable medium, comprising:
    code for causing a computer to receive measurement values of one or more specimen parameters associated with a model based measurement of one or more metrology targets by a target measurement system;
    code for causing the computer to receive reference measurement values of the same one or more specimen parameters associated with a measurement of the same one or more metrology targets by a reference measurement source that differs from the model based measurement of the one or more metrology targets by the target measurement system; and
    code for causing the computer to determine one or more parameters of a meta-model that transforms the measurement values of the one or more specimen parameters to corrected measurement values of the one or more specimen parameters, wherein the determining of the one or more parameters of the meta-model involves minimizing a difference between the reference measurement values and the corrected measurement values of the one or more specimen parameters.

11. The non-transitory, computer-readable medium of claim 10, further comprising:
    code for causing the computer to receive measurement values of the same one or more specimen parameters associated with a model based measurement of another metrology target by the target measurement system;
    code for causing the computer to determine corrected measurement values of the same one or more specimen parameters associated with the model based measurement of the other metrology target by the target measurement system based at least in part on a transformation of the received measurement values by the meta-model; and
    code for causing the computer to store the corrected measurement values of the same one or more specimen parameters associated with the model based measurement of the other metrology target in a memory.

12. The non-transitory, computer-readable medium of claim 10, wherein the measurement values of the one or more specimen parameters are estimated by the target measurement system based on any of an amount of synthetic measurement data and an amount of actual measurement data.

13. The non-transitory, computer-readable medium of claim 12, wherein the measurement values of the one or more specimen parameters are estimated by the target measurement system using any of a library function and a regression of a measurement model.

14. The non-transitory, computer-readable medium of claim 12, wherein the reference measurement values of the same one or more specimen parameters are estimated based on any of an amount of synthetic reference measurement data and an amount of actual reference measurement data.

15. The non-transitory, computer-readable medium of claim 14, wherein the reference measurement values of the same one or more specimen parameters are estimated using any of a reference library function and a regression of a reference measurement model.

16. The non-transitory, computer-readable medium of claim 10, wherein the measurement values of the one or more specimen parameters are estimated by the target measurement system based on an amount of measurement data that is a subset of an amount of reference measurement data.

17. The non-transitory, computer-readable medium of claim 10, wherein the determining of the one or more parameters of the meta-model involves any of a neural network optimization, a support vector machine optimization, and a nonlinear least squares optimization.

18. An apparatus comprising:
    an illumination source;
    a detector; and
    one or more computer systems configured to:
        receive measurement values of one or more specimen parameters associated with a model based measurement of one or more metrology targets by a target measurement system;
        receive reference measurement values of the same one or more specimen parameters associated with a measurement of the same one or more metrology targets by a reference measurement source that differs from the model based measurement of the one or more metrology targets by the target measurement system; and
        determine one or more parameters of a meta-model that transforms the measurement values of the one or more specimen parameters to corrected measurement values of the one or more specimen parameters, wherein the determining of the one or more parameters of the meta-model involves minimizing a difference between the reference measurement values and the corrected measurement values of the one or more specimen parameters.

19. The apparatus of claim 18, wherein the one or more computer systems is further configured to:
    receive measurement values of the same one or more specimen parameters associated with a model based measurement of another metrology target by the target measurement system;
    determine corrected measurement values of the same one or more specimen parameters associated with the model based measurement of the other metrology target by the target measurement system based at least in part on a transformation of the received measurement values by the meta-model; and
    store the corrected measurement values of the same one or more specimen parameters associated with the model based measurement of the other metrology target in a memory.

20. The apparatus of claim 18, wherein the measurement values of the one or more specimen parameters are estimated by the target measurement system based on an amount of measurement data that is a subset of an amount of reference measurement data.

* * * * *